United States Patent [19]

Husain

[11] Patent Number: 4,992,578
[45] Date of Patent: Feb. 12, 1991

[54] PREPARATION OF ALKYL ALKANETHIOLSULFONATES

[75] Inventor: Altaf Husain, East Norriton, Pa.

[73] Assignee: Atochem North America, Inc., Philadelphia, Pa.

[21] Appl. No.: 491,407

[22] Filed: Mar. 9, 1990

[51] Int. Cl.$^5$ .......................................... C07C 143/00
[52] U.S. Cl. ..................................................... 560/307
[58] Field of Search ......................................... 560/307

[56] References Cited

U.S. PATENT DOCUMENTS 3,153,078 0/1964 Fierce et al. ...................... 560/307
3,365,480 0/1968 Cobb et al. ....................... 560/307
3,670,002 0/1972 Sheng et al. ...................... 560/307

OTHER PUBLICATIONS

Chem. Abstract 76:3397q (1972), abstracting French Patent 2,044,265.
Nogami et al., Chem. Pharm. Bull., 19(12), 2472-77 (1971).
Chem. Abstract 101:110070j (1984) abstracting Machion et al., An. Simp. Bras. Electroquim. Electroanal., 4th 289-292 (1984).
Chem. Abstract 100:8766b (1984), abstracting Polish PL 117,553.
Bhattacharya et al., J. Org. Chem., 43(13), 2728-2730 (1978).

Primary Examiner—Nicky Chan
Attorney, Agent, or Firm—Seidel, Gonda, Lavorgna & Monaco

[57] ABSTRACT

Alkyl alkanethiolsulfonates are prepared by oxidation of the corresponding alkanethiol, dialkyl disulfide, or mixture thereof by aqueous hydrogen peroxide in the presence of a Group VIII transition metal catalyst.

23 Claims, No Drawings

PREPARATION OF ALKYL ALKANETHIOLSULFONATES

FIELD OF THE INVENTION

This invention relates to the manufacture of alkyl alkanethiolsulfonates by the oxidation of the corresponding alkanethiol or dialkyl disulfide. More specifically, it relates to the oxidation of such compounds by hydrogen peroxide in the presence of a Group VIII transition metal catalyst to form the corresponding alkyl alkanethiolsulfonate.

BACKGROUND OF THE INVENTION

Alkyl alkanethiolsulfonates have been prepared by electrochemical oxidation of the corresponding alkyl disulfide (CA 101:110070j (1984), abstract Machion et al., *An. Simo. Bras. Electroquim. Electroanal.*, 4th, 289-292 (1984)) and electrochemical reduction of the corresponding sulfonyl chloride and sodium salt of the sulfonic acid (CA 100:87666b (1984), abstracting Polish PL 117,553).

Various oxidizing agents have been employed in the preparation of alkyl alkanethiolsulfonates from the corresponding disulfides. These include, m-chloroperbenzoic acid (Bhattacharya et al., *J. Org. Chem.* 43(13) 2728-2730 (1978)); organic hydroperoxide in the presence of a Mo(VI)-containing catalyst (U.S. Pat. No. 3,670,002); air in the presence of various transition metal halides and oxyhalides (CA 76:3397q (1972), abstracting French Patent No. 2,044,265); and nitrogen dioxide (U.S. Pat. No. 3,153,078).

U.S. Pat. No. 3,365,480 describes the preparation of various nitrogen-containing thiolsulfonates by the oxidation of the acid salts of the corresponding disulfide with hydrogen peroxide in a polar solvent such as an alcohol or an organic acid. Propyl propanethiolsulfonate has been identified by thin layer chromatography in the product mixture resulting from the oxidation of dipropyl disulfide by hydrogen peroxide in acetic acid solution (Nogami et al., *Chem. Pharm. Bull.* 19(12), 2472-77 (1971)). In cases where an organic solvent such as acetic acid is employed in conjunction with hydrogen peroxide, the de facto oxidizing agent is likely to be the corresponding peracid. In such instances, and, in general, when an organic solvent is employed, there is a need to recover and recycle the solvent to make the process economic.

In other prior art processes, exotic and expensive oxidizing agents such as m-chloroperbenzoic acid, sodium metaperiodate, and the like are utilized. Commercial application of such processes is questionable.

SUMMARY OF THE INVENTION

The invention described herein is a process for preparing an alkyl alkanethiolsulfonate by contacting the corresponding alkanethiol, dialkyl disulfide or mixture thereof with aqueous hydrogen peroxide in the presence of one or more transition metal catalysts selected from the Group VIII elements of the Periodic Table of the Elements.

DETAILED DESCRIPTION OF THE INVENTION

Alkanethiols, dialkyl disulfides or mixture thereof are oxidized by aqueous hydrogen peroxide in the presence of a catalytic amount of one or more Group VIII transition metal catalysts. An advantage of the process of the present invention is that it uses a heterogeneous catalytic system. The process can be operated in a batchwise manner in which case the catalyst can be easily removed from the product mixture by filtration and recycled. If desired, the process can also be operated in a continuous manner by using a fixed bed of the heterogeneous catalyst.

Without wishing to be bound by any theory, it is believed that the alkyl alkanethiolsulfonate corresponding to the starting alkanethiol or dialkyl disulfide is prepared according to the following proposed chemical equations:

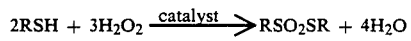

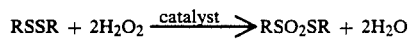

The alkanethiols which may be converted to their corresponding alkyl alkanethiolsulfonates in the process of the invention typically may have 1-18 carbon atoms, preferably 1-8 carbon atoms. Thus, there may be used, for example, methanethiol, ethanethiol, n-propanethiol, isopropanethiol, 1-butanethiol, 2-butanethiol, 1-hexanethiol, 1-octanethiol or 1-decanethiol.

The dialkyl disulfides which may be converted to their corresponding alkyl alkanethiolsulfonates according to the present invention, typically may have 2-20 carbon atoms, preferably 2-16 carbon atoms. Thus, there may be used, for example, dimethyl disulfide, diethyl disulfide, dipropyl disulfide, diisopropyl disulfide, dibutyl disulfide, diamyl disulfide, dihexyl disulfide, dioctyl disulfide, or didecyl disulfide.

The catalyst that can be employed in the process of the present invention is a transition metal chosen from among the metals of Group VIII of the Periodic Table of the Elements, preferably selected from the group of iridium, palladium, platinum, rhodium, and mixtures thereof. The catalyst can be employed either in the form of pure metal, i.e., pure powdered metal, or is alternatively loaded on an inert solid support. The solid support may comprise, for example, a metal oxide such as alumina, silica, titania, zirconia or a mixture thereof. The catalyst may be in the form of a powder, pellets, or any other convenient form.

When the catalyst is in the form of a metal loaded onto a support, the loading may advantageously be in the range of from about 1 weight percent to about 20 weight percent metal, based upon the weight of the entire supported catalyst, including the support. Preferably the loading is from about 2 to about 10 weight percent.

The amount of metal catalyst used in the process of the invention may advantageously range from about 0.1 to about 5.0 g of metal per mole of the alkanethiol or dialkyl disulfide. Preferably, the metal catalyst is present in the range of from about 0.2 to about 2.0 g of metal per mole of the alkanethiol or dialkyl disulfide.

The concentration of hydrogen peroxide in the aqueous hydrogen peroxide solution can range from about 3 weight percent to about 90 weight percent. However, concentrations of from about 30 weight percent to about 70 weight percent hydrogen peroxide are preferred, because of the ready availability of solutions of this concentration.

The amount of hydrogen peroxide contacted with the alkanethiol or dialkyl disulfide can range from about 1 to about 10 moles of hydrogen peroxide for each mole of alkanethiol or dialkyl disulfide. Preferably, the amount of hydrogen peroxide contacted is from about 2 to about 6 moles for each mole of dialkyl disulfide, or from about 3 to about 6 moles for each mole of alkanethiol.

The temperature at which the process of the invention is carried out can vary over a broad range. Typically, the temperature may be from about 25° C. to about 100° C. Preferably, the temperature is from about 40° C. to about 60° C.

The reaction time, that is, the time during which the reactants and catalyst are in contact, is selected such as to obtain maximum conversion of the alkanethiol or dialkyl disulfide to the corresponding alkyl alkanethioltetsulfonate. Although the reaction time selected depends of course, upon several factors such as the reaction temperature, the amount of catalyst used, and the efficiency of agitation of the reaction mixture, the reaction time is generally between about one hour and about four hours.

The process of this invention can be carried out in a batchwise or a continuous manner. In the batchwise manner, the reaction vessel is charged with either the alkanethiol or the dialkyl disulfide, or a mixture thereof, and the catalyst and brought up to the desired temperature. Aqueous hydrogen peroxide is added over a selected time period, while maintaining the reaction mixture at the desired temperature. The contents are preferably vigorously agitated to give maximum mixing of the reactants. After the completion of the hydrogen peroxide addition, the reaction mixture is further agitated and maintained at the desired temperature for a period of time sufficient to achieve the maximum yield of the alkanethiolsulfonate.

In the continuous mode of operation, the alkanethiol, dialkyl disulfide or mixture thereof, and the aqueous hydrogen peroxide are continuously fed to a reaction zone containing the catalyst, wherein the reactants are reacted at the desired temperature. The reaction mixture containing the desired alkyl alkanethiolsulfonate is continuously removed from the reaction zone at a rate so as to give a maximum yield of the corresponding alkyl alkanethiolsulfonate. The alkyl alkanethiolsulfonate is then separated from the unreacted alkanethiol or dialkyl disulfide and the catalyst in a manner known to those skilled in this art. The unreacted alkanethiol or dialkyl disulfide and catalyst may be recycled to the reactor.

The process of this invention is demonstrated by, but not limited to, the following illustrative examples.

Example 1

To a well-stirred mixture of dimethyl disulfide (9.47 g; 100 mmole) and 1.0 g of a catalyst consistinq of alumina loaded with 5% rhodium, was added 30% hydrogen peroxide (66.7 g; 588 moles) over the course of 35 minutes, while maintaining the temperature of the reaction mixture at 50°-60° C. Upon completing the addition of the hydrogen peroxide, the reaction mixture was agitated for an additional one hour while maintaining the temperature at 50° C. The reaction mixture was then cooled, filtered to remove the catalyst, and extracted with three 25 ml portions of methylene chloride. Analysis of the methylene chloride extract by gas chromatography indicated the formation of 8.9 g (70.1% yield) of methyl methanethiolsulfonate.

Example 2

To a well-stirred mixture of dimethyl disulfide (9.36 g; 99.6 mmole) and 0.1 g of powdered palladium black, was added 30% hydrogen peroxide (66.7 g; 588 moles) over 40 minutes, while maintaining the temperature of the reaction mixture at 50°-60° C. Upon completing the addition of the hydrogen peroxide, the reaction mixture was agitated for an additional one and one half hour while maintaining the temperature at 50°-60° C. The reaction mixture was then cooled, filtered and extracted with three 25 ml portions of methylene chloride. Analysis of the methylene chloride extract by gas chromatography indicated the formation of 8.3 g (66.5% yield) of methyl methanethiolsulfonate.

Example 3

To a well-stirred mixture of n-propanethiol (15.3 g; 200 mmole) and 1.0 g of a catalyst consisting of alumina loaded with 5% rhodium, was added 30% hydrogen peroxide (66.7 g; 588 moles) over 1 hour, while maintaining the temperature of the reaction mixture at 50° C. After the completion of the addition the reaction mixture was agitated for an additional one hour while maintaining the temperature at 50° C. The reaction mixture was then cooled, filtered, and extracted with three 25 ml portions of toluene. Analysis of the toluene extract by gas chromatography indicated the formation of 1.6 g (9.0% yield) of propyl propanethiolsulfonate and 5.6 g (37.0% yield) of dipropyl disulfide.

The present invention may be embodied in other specific forms without departing from the spirit or essential attributes thereof and, accordingly, reference should be made to the appended claims, rather than to the foregoing specification, as indicating the scope of the invention.

I claim:

1. A process for preparing an alkyl alkanethiolsulfonate comprising contacting the corresponding alkanethiol, dialkyl disulfide or mixture thereof with aqueous hydrogen peroxide in the presence of one or more transition metal catalysts selected from the Group VIII elements of the Periodic Table of the Elements.

2. The process of claim 1 wherein the metal catalyst is selected from the group of iridium, palladium, platinum, rhodium, and mixtures thereof.

3. The process of claim 1 wherein the metal catalyst comprises pure powdered metal or metal supported on an inert support.

4. The process according the claim 3 wherein the catalyst is supported on an inert support selected from the group of alumina, silica, titania, zirconia, or a combination thereof.

5. The process of claim 3 wherein the alkanethiol has 1 to 18 carbon atoms, and the dialkyl disulfide has 2 to 20 carbon atoms.

6. The process of claim 5 wherein the alkanethiol has 1 to 8 carbon atoms, and the dialkyl disulfide has 2 to 16 carbon atoms.

7. The process of claim 5 wherein the amount of metal catalyst is from about 0.1 g to about 5.0 g of metal per mole of alkanethiol or dialkyl disulfide.

8. The process of claim 7 wherein the amount of metal catalyst is from about 0.2 to about 2.0 g of metal per mole of alkanethiol or dialkyl disulfide.

9. The process of claim 7 wherein the metal catalyst is supported on an inert support and the concentration of the metal in the supported catalyst is from about 1 to about 20 weight percent.

10. The process of claim 9 wherein the concentration of the metal in the supported catalyst is from about 2 to about 10 weight percent.

11. The process of claim 5 wherein the amount of hydrogen peroxide is from about to about 10 moles per mole of alkanethiol or dialkyl disulfide.

12. The process of claim 11 wherein an alkanethiol is contacted with aqueous hydrogen peroxide, and the amount of hydrogen peroxide is from about 2 to about 6 moles per mole of alkanethiol.

13. The process of claim 11 wherein a dialkyl disulfide is contacted with aqueous hydrogen peroxide, and the amount of hydrogen peroxide is from about 3 to about 6 moles per mole of dialkyl disulfide.

14. The process of claim 11 wherein the hydrogen peroxide is in the form of an aqueous solution having a hydrogen peroxide concentration of from about 3 to about 90 weight percent, based on the weight of the solution.

15. The process of claim 14 wherein the hydrogen peroxide concentration is from about 30 to about 70 weight percent, based on the weight of the solution.

16. The process of claim 11 wherein the reaction temperature is from about 25° C. to about 100° C.

17. The process of claim 16 wherein the reaction temperature is from about 40° C. to about 60° C.

18. The process of claim 5 wherein the alkyl alkanethiolsulfonate product comprises methyl methanethiolsulfonate.

19. The process of claim 5 wherein the alkyl alkanethiolsulfonate product comprises propyl propanethiolsulfonate.

20. A process for preparing an alkyl alkanethiolsulfonate comprising contacting an alkanethiol containing 1 to 18 carbon atoms, a dialkyl disulfide containing 2 to 20 carbon atoms, or a mixture thereof with from about 1 to about 10 moles of aqueous hydrogen peroxide per mole of alkanethiol or dialkyl disulfide, in the presence of one or more Group VIII metal catalysts containing from about 0.1 g to about 5.0 g of said Group VIII metal per mole of alkanethiol or dialkyl disulfide.

21. The process of claim 20 wherein the metal catalyst is selected from the group of palladium, platinum, rhodium, and mixtures thereof.

22. The process of claim 21 wherein the reaction temperature is from about 25° C. to about 100° C.

23. A continuous process for producing an alkyl alkanethiolsulfonate comprising continuously feeding aqueous hydrogen peroxide and an alkanethiol, dialkyl disulfide, or mixture thereof, to a reaction zone containing a Group VIII transition metal catalyst, reacting said hydrogen peroxide with said alkanethiol or dialkyl disulfide in the reaction zone, and continuously removing from the reaction zone a reaction mixture containing the alkyl alkanethiolsulfonate.

* * * * *